(12) United States Patent
Bachmann et al.

(10) Patent No.: US 10,238,592 B2
(45) Date of Patent: Mar. 26, 2019

(54) ORGANIC COMPOUNDS

(71) Applicant: GIVAUDAN SA, Vernier (CH)

(72) Inventors: Jean-Pierre Bachmann, Waedenswil (CH); Felix Flachsmann, Duebendorf (CH); Roger Wilhelm Geiser, Zurich (CH); Matias Mueller, Daettlikon (CH); Christian Quellet, Biel (CH)

(73) Assignee: GIVAUDAN S.A., Vernier (CH)

( * ) Notice: Subject to any disclaimer, the term of this patent is extended or adjusted under 35 U.S.C. 154(b) by 44 days.

(21) Appl. No.: 15/300,148

(22) PCT Filed: Apr. 28, 2015

(86) PCT No.: PCT/EP2015/000866
§ 371 (c)(1),
(2) Date: Sep. 28, 2016

(87) PCT Pub. No.: WO2015/165582
PCT Pub. Date: Nov. 5, 2015

(65) Prior Publication Data
US 2017/0181945 A1 Jun. 29, 2017

(30) Foreign Application Priority Data
Apr. 28, 2014 (GB) .................................. 1407383.7

(51) Int. Cl.
*A61K 8/40* (2006.01)
*A61Q 13/00* (2006.01)
*C11D 3/50* (2006.01)

(52) U.S. Cl.
CPC ............. *A61K 8/40* (2013.01); *A61Q 13/00* (2013.01); *C11D 3/50* (2013.01); *A61K 2800/592* (2013.01)

(58) Field of Classification Search
CPC .................................. A61Q 13/00; C11B 9/00
See application file for complete search history.

(56) References Cited

U.S. PATENT DOCUMENTS

| 6,069,125 A | 5/2000 | Pesaro |
| 8,481,789 B2 | 7/2013 | Mane |
| 2010/0063011 A1* | 3/2010 | Natsch .................... A61K 8/33 514/166 |

FOREIGN PATENT DOCUMENTS

| EP | 1890999 | 2/2008 |
| EP | 1968531 | 9/2008 |
| EP | 2708592 A1 | 3/2014 |
| WO | 2006133592 A1 | 12/2006 |
| WO | 2007030961 A3 | 3/2007 |

OTHER PUBLICATIONS

GB Search Report for corresponding application GB 1407383.7 dated Mar. 9, 2015.
International Search Report and Written Opinion of the International Searching Authority for corresponding application PCT/EP2015/000866 dated Sep. 23, 2015.

* cited by examiner

*Primary Examiner* — Arrie L Reuther
(74) *Attorney, Agent, or Firm* — Norris McLaughlin PA

(57) ABSTRACT

A liquid fragrance composition consisting essentially of:
cyclohexylidene phenyl acetonitrile; and
one or more ingredients selected from the group consisting of cyclohexyl salicylate, MEFROSOL™ (3-methyl-5-phenyl-pentan-1-ol), HEDIONE™ (methyl 2-(3-oxo-2-pentylcyclopentyl)acetate), diethyl phthalate, isopropyl myristate, amyl salicylate, iso-amyl salicylate, benzyl salicylate, iso-bornyl salicylate, cis-3 hexenyl salicylate, ethyl salicylate, iso-butyl salicylate, methyl salicylate and phenylethyl salicylate; and optionally
one or more of 3-methyl-5-phenylpentan-1-ol (MEFROSOL™); an alcohol comprising more than 3 carbon atoms selected from the group consisting of benzyl alcohol, 1-hexanol, 1-heptanol, 1-octanol, cyclohexanol, cyclohexyl propanol, methyl phenyl carbinol, phenyl ethyl alcohol and dimethyl benzyl carbinol; or a glycol ether.

14 Claims, No Drawings

ORGANIC COMPOUNDS

This patent application claims the full priority benefit of PCT/EP2015/000866 filed 28 Apr. 2015, and to the earlier filed priority application, GB 1407383.7 filed 28 Apr. 2014. The entirety of the foregoing documents are herein incorporated by reference.

The present invention relates to stock solutions containing cyclohexylidene phenyl acetonitrile, and to consumer products containing same.

Cyclohexylidene phenyl acetonitrile (known more commonly by the name PEONILE™) is a highly valued perfume ingredient, having an odour that has been characterised as flowery-rosy, green, metallic, and reminiscent of geranium. PEONILE™ is powerful, relatively non-volatile and is very stable in almost all media. It has very high substantivity on wet and dry laundry and helps to increase volume and tenacity in functional perfumes. Accordingly, it has been widely used in all manner of consumer products from fine fragrances, through cosmetics, personal care and household care products. The molecule, and its use as an odourant, are described in U.S. Pat. No. 6,069,125.

Despite the considerable commercial success of this molecule, we have found that it is not always a straightforward matter to blend it with other perfume ingredients. In particular, applicant has found that under certain conditions of storage at low temperatures, cyclohexylidene phenyl acetonitrile will crystallise. In particular, crystallisation can occur at temperatures below about 28 degrees centigrade, particularly when the liquid comes into contact with irregular packaging surfaces or solid impurities. Crystallisation leads to very rapid solidification of the bulk material and the only remedy available to the formulator hoping to blend the material with other ingredients is to heat the container in which it is stored. This adds to processing time and costs, and, when the heating step is not carried out carefully, can lead to the development of undesirable burnt off-notes.

The melting point of a specific target substance can be depressed by mixing it with a second substance, which second substance has i) a lower melting point, or ii) forms a eutectic mixture with the target substance. However, whereas there may be many ingredients that can depress the melting point of a target substance, the target substance and the second substance must be thermodynamically compatible (i.e. they should not phase separate) across the entire temperature range within which one requires a liquid state. Still further, liquid mixtures that are thermodynamically compatible below their liquid-solid phase separation temperature, must remain so even if an impurity is inadvertently or deliberately added to the liquid mixture, or if the liquid mixture is brought into contact with a surface, which could create crystal nucleation sites.

An additional requirement in the field of perfumery is that the mixture of the target substance and the second substance must be olfactively acceptable from a perfumery standpoint, that is, the mixture of substances should have an odour direction and odour intensity that is substantially similar to the pure target substance.

The matter of discovering suitable ingredients to combine with cyclohexylidene phenyl acetonitrile in order to provide a liquid composition, which meet the aforementioned requirements was not straightforward. For example, the skilled person might predict that the fragrance ingredient PETALIA™, which is structurally very similar to cyclohexylidene phenyl acetonitrile, might produce a thermodynamically compatible eutectic mixture, which would remain liquid down to low temperature and which would also be very advantageous because of the similar olfactive direction of cyclohexylidene phenyl acetonitrile and PETALIA™. However, this was found not to be the case. The skilled person might also predict that a broad selection of liquid organic substances, such as liquid fragrance materials and solvents might produce thermodynamically compatible binary mixtures with cyclohexylidene phenyl acetonitrile over broad temperature ranges. However, this was also found not to be the case. In particular, other perfume ingredients having a similar olfactive direction to cyclohexylidene phenyl acetonitrile such as phenyl ethyl alcohol, phenoxy ethyl alcohol, ROSE OXIDE™, SUPER MUGUET™ (6-ethyl-3-methyl-6-octen-1-ol), dimethyl benzyl carbinol, POMAROSE™ (5,6,7-trimethyl-2,5-octadiene-4-one), PIVAROSE™ (phenyl ethyl 2,2-dimethylpropanoate), PEOMOSA™ (2-methyphenyl ethyl alcohol), ROSAPHEN™ (2methyl-5-phenyl-pentan-1-ol) PELARGENE™ (2-methyl-4-methylene-6-phenyl-tetrahydro-2H-pyran), diphenyl oxide, GERANODYLE™ (1-hydroxy-2-(1-methyl-1-hydroxyethyl)-5-methylcyclohexane), 3-methyl-2-phenylbut-2-enenitrile, 3-ethyl-2-phenylpent-2-enenitrile or (Z)-2-phenylhex-2-enenitrile, were also unable to form thermodynamically compatible liquid binary compositions with cyclohexylidene phenyl acetonitrile. Still further, lower alcohols such as ethanol and iso-propyl alcohol; and glycol ethers, such as propylene glycol, dipropylene glycol, DOWANOL PM™ or DOWANOL™ DPM were also not suitable materials to admix with cyclohexylidene phenyl acetonitrile in compatible binary mixtures.

The present application addresses the potential issues related to the handling and storage of cyclohexylidene phenyl acetonitrile, and overcomes them by providing in a first aspect a liquid fragrance composition consisting essentially of:
  cyclohexylidene phenyl acetonitrile; and
  a component A, which is one or more ingredients selected from the group consisting of cyclohexyl salicylate, MEFROSOL™ (3-methyl-5-phenyl-pentan-1-ol), HEDIONE™ (methyl 2-(3-oxo-2-pentylcyclopentyl) acetate), diethyl phthalate, isopropyl myristate, amyl salicylate, iso-amyl salicylate, benzyl salicylate, isobornyl salicylate, cis-3 hexenyl salicylate, ethyl salicylate, iso-butyl salicylate, methyl salicylate, phenylethyl salicylate and KARMAFLOR ((Z)-hept-4-en-2-yl salicylate); and optionally
  a component B, which is one or more of ROSE OXIDE™, SUPER MUGUET™ (6-ethyl-3-methyl-6-octen-1-ol), dimethyl benzyl carbinol, POMAROSE™ (5,6,7-trimethyl-2,5-octadiene-4-one), PIVAROSE™ (phenyl ethyl 2,2-dimethylpropanoate), PEOMOSA™ (2-methyphenyl ethyl alcohol), ROSAPHEN™ (2methyl-5-phenyl-pentan-1-ol) PELARGENE™ (2-methyl-4-methylene-6-phenyl-tetrahydro-2H-pyran), diphenyl oxide, GERANODYLE™ (1-hydroxy-2-(1-methyl-1-hydroxyethyl)-5-methylcyclohexane), 3-methyl-2-phenylbut-2-enenitrile, 3-ethyl-2-phenylpent-2-enenitrile or (Z)-2-phenylhex-2-enenitrile; an alcohol comprising more than 3 carbon atoms selected from the group consisting of benzyl alcohol, 1-hexanol, 1-heptanol, 1-octanol, cyclohexanol, cyclohexyl propanol, methyl phenyl carbinol, phenyl ethyl alcohol and dimethyl benzyl carbinol; a glycol ether.

In a particular embodiment of the present invention the liquid fragrance composition consists essentially of:
  cyclohexylidene phenyl acetonitrile; and
  a component A, which is one or more ingredients selected from the group consisting of cyclohexyl salicylate, MEFROSOL™ (3-methyl-5-phenyl-pentan-1-ol), HEDIONE™ (methyl 2-(3-oxo-2-pentylcyclopentyl) acetate), diethyl phthalate, isopropyl myristate, amyl salicylate, iso-amyl salicylate, benzyl salicylate, iso-bornyl salicylate, cis-3 hexenyl salicylate, ethyl salicylate, iso-butyl salicylate, methyl salicylate and phenylethyl salicylate and KARMAFLOR ((Z)-hept-4-en-2-yl salicylate).

In yet another embodiment of the present invention, the liquid fragrance composition consists essentially of:
cyclohexylidene phenyl acetonitrile; and
a component A, which is a salicylate selected from the group consisting of cyclohexyl salicylate, benzyl salicylate, iso-bornyl salicylate and phenylethyl salicylate.

In yet another embodiment of the present invention, the liquid fragrance composition consists essentially of:
cyclohexylidene phenyl acetonitrile; and
a component A, which is an ingredient selected from the group consisting of cyclohexyl salicylate, MEFROSOL™ (3-methyl-5-phenyl-pentan-1-ol), HEDIONE™ (methyl 2-(3-oxo-2-pentylcyclopentyl) acetate), diethyl phthalate, isopropyl myristate, amyl salicylate, iso-amyl salicylate, benzyl salicylate, iso-bornyl salicylate, cis-3 hexenyl salicylate, ethyl salicylate, iso-butyl salicylate, methyl salicylate, phenylethyl salicylate and KARMAFLOR ((Z)-hept-4-en-2-yl salicylate); and
a component B, which is one or more of 3-methyl-5-phenylpentan-1-ol (MEFROSOL™), ROSE OXIDE™, SUPER MUGUET™ (6-ethyl-3-methyl-6-octen-1-ol), dimethyl benzyl carbinol, POMAROSE™ (5,6,7-trimethyl-2,5-octadiene-4-one), PIVAROSE™ (phenyl ethyl 2,2-dimethylpropanoate), PEOMOSA™ (2-methyphenyl ethyl alcohol), ROSAPHEN™ (2methyl-5-phenyl-pentan-1-ol) PELARGENE™ (2-methyl-4-methylene-6-phenyl-tetrahydro-2H-pyran), diphenyl oxide, GERANODYLE™ (1-hydroxy-2-(1-methyl-1-hydroxyethyl)-5-methylcyclohexane), 3-methyl-2-phenylbut-2-enenitrile, 3-ethyl-2-phenylpent-2-enenitrile or (Z)-2-phenylhex-2-enenitrile; an alcohol comprising more than 3 carbon atoms selected from the group consisting of benzyl alcohol, 1-hexanol, 1-heptanol, 1-octanol, cyclohexanol, cyclohexyl propanol, methyl phenyl carbinol, phenyl ethyl alcohol and dimethyl benzyl carbinol; or a glycol ether.

In yet another embodiment of the present invention, the liquid fragrance composition consists essentially of:
cyclohexylidene phenyl acetonitrile; and
a component A, which is an ingredient selected from the group consisting of cyclohexyl salicylate, MEFROSOL™ (3-methyl-5-phenyl-pentan-1-ol), HEDIONE™ (methyl 2-(3-oxo-2-pentylcyclopentyl) acetate), diethyl phthalate, isopropyl myristate, amyl salicylate, iso-amyl salicylate, benzyl salicylate, iso-bornyl salicylate, cis-3 hexenyl salicylate, ethyl salicylate, iso-butyl salicylate, methyl salicylate, phenylethyl salicylate and KARMAFLOR ((Z)-hept-4-en-2-yl salicylate); and
a component B, which is 3-methyl-5-phenylpentan-1-ol (MEFROSOL™) ROSE OXIDE™, SUPER MUGUET™ (6-ethyl-3-methyl-6-octen-1-ol), dimethyl benzyl carbinol, POMAROSE™ (5,6,7-trimethyl-2,5-octadiene-4-one), PIVAROSE™ (phenyl ethyl 2,2-dimethylpropanoate), PEOMOSA™ (2-methyphenyl ethyl alcohol), ROSAPHEN™ (2methyl-5-phenyl-pentan-1-ol) PELARGENE™ (2-methyl-4-methylene-6-phenyl-tetrahydro-2H-pyran), diphenyl oxide, GERANODYLE™ (1-hydroxy-2-(1-methyl-1-hydroxyethyl)-5-methylcyclohexane), 3-methyl-2-phenylbut-2-enenitrile, 3-ethyl-2-phenylpent-2-enenitrile or (Z)-2-phenylhex-2-enenitrile; an alcohol comprising more than 3 carbon atoms selected from the group consisting of benzyl alcohol, 1-hexanol, 1-heptanol, 1-octanol, cyclohexanol, cyclohexyl propanol, methyl phenyl carbinol, phenyl ethyl alcohol and dimethyl benzyl carbinol; or a glycol ether.

As used herein, the term "glycol ether" includes compounds selected from the group consisting of propylene glycol, dipropylene glycol, 1-methoxy-2-propanol DOWANOL™ PM or 2-(2-methoxypropoxy)propan-1-ol DOWANOL™ DPM.

In a particular embodiment of the present invention, the liquid fragrance composition consists essentially of cyclohexylidene phenyl acetonitrile; and cyclohexyl salicylate or benzyl salicylate or iso-bornyl salicylate or phenylethyl salicylate and optionally 3-methyl-5-phenylpentan-1-ol (MEFROSOL™).

In a particular embodiment of the present invention, the liquid fragrance composition consists essentially of cyclohexylidene phenyl acetonitrile; and cyclohexyl salicylate or benzyl salicylate or iso-bornyl salicylate or cyclohexyl salicylate or phenylethyl salicylate; and optionally benzyl alcohol or 1-hexanol, 1-heptanol or 1-octanol or cyclohexanol or methyl phenyl carbinol or phenyl ethyl alcohol or dimethyl benzyl carbinol.

In a particular embodiment of the present invention, the liquid fragrance composition consists essentially of cyclohexylidene phenyl acetonitrile; and cyclohexyl salicylate or benzyl salicylate or iso-bornyl salicylate or phenylethyl salicylate; and optionally a glycol ether, still more particularly, wherein the glycol ether is propylene glycol or dipropylene glycol or 1-methoxy-2-propanol DOWANOL™ PM or 2-(2-methoxypropoxy)propan-1-ol DOWANOL™ DPM.

In a particular embodiment of the present invention, the liquid fragrance composition consists essentially of:
cyclohexylidene phenyl acetonitrile;
and a component A, which is a salicylate selected from the group consisting of cyclohexyl salicylate, amyl salicylate, iso-amyl salicylate, benzyl salicylate, iso-bornyl salicylate, cis-3 hexenyl salicylate, ethyl salicylate, iso-butyl salicylate, methyl salicylate, phenylethyl salicylate and KARMAFLOR ((Z)-hept-4-en-2-yl salicylate); and
one of MEFROSOL™ (3-methyl-5-phenyl-pentan-1-ol), HEDIONE™ (methyl 2-(3-oxo-2-pentylcyclopentyl) acetate), diethyl phthalate, isopropyl myristate, ROSE OXIDE™, or SUPER MUGUET™ (6-ethyl-3-methyl-6-octen-1-ol), or dimethyl benzyl carbinol, or POMAROSE™ (5,6,7-trimethyl-2,5-octadiene-4-one), or PIVAROSE™ (phenyl ethyl 2,2-dimethylpropanoate), or PEOMOSA™ (2-methyphenyl ethyl alcohol), or ROSAPHEN™ (2methyl-5-phenyl-pentan-1-ol), or PELARGENE™ (2-methyl-4-methylene-6-phenyl-tetrahydro-2H-pyran), or diphenyl oxide, or GERANODYLE™ (1-hydroxy-2-(1-methyl-1-hydroxyethyl)-5-methylcyclohexane), or 3-methyl-2-phenylbut-2-enenitrile, or 3-ethyl-2-phenylpent-2-enenitrile or (Z)-2-phenylhex-2-enenitrile.

Where trivial names or trade names are used to describe perfume ingredients herein, the skilled perfumer will understand that these are commonly used names by perfumers. However, the skilled perfumer will also understand that these ingredients may also be known by other trivial synonyms, by CAS registry numbers, or by more formal nomenclature, such as IUPAC nomenclature. Furthermore, the skilled perfumer will be familiar with these synonyms, as well as with more formal nomenclature, or at the least, would be aware of standard reference works, such as The Good Scent Company web site, which contains a comprehensive list of relationships between trivial names, registry numbers and more formal nomenclature for all manner of perfume ingredients contained on the perfumers palette.

In a liquid fragrance composition of the present invention, the amount of cyclohexylidene phenyl acetonitrile present may be about 40 to about 95% by weight, based on the total weight of the composition.

In a liquid fragrance composition of the present invention, the amount of component A is present between about 5 to about 60 wt % of the liquid fragrance composition, and more particularly 10 and 60 wt %, still more particularly 20 to 60 wt % of the composition, still more particularly 25 to 55 wt % of the composition and still more particularly 45 to 55 wt %.

In a liquid fragrance composition of the present invention, the amount of component B is present between about 5 to about 25% by weight of the liquid fragrance composition.

A particular liquid fragrance composition of the present invention consist of cyclohexylidene phenyl acetonitrile (40 to 95 weight % and more particularly 45 to 55 weight %); and cyclohexyl salicylate (20 to 60 weight %, and more particularly 45 to 55 weight %).

Yet another particular liquid fragrance composition of the present invention consist of
cyclohexylidene phenyl acetonitrile (40 to 95 weight % and more particularly 45 to 55 weight %); and cyclohexyl salicylate (20 to 60 weight %, and more particularly 45 to 55 weight %); and
benzyl alcohol (5 to 25 weight %, and more particularly 10 weight %).

Yet another particular liquid fragrance composition of the present invention consist of
cyclohexylidene phenyl acetonitrile (40 to 95 weight % and more particularly 45 to 55 weight %); and cyclohexyl salicylate (20 to 60 weight %, and more particularly 45 to 55 weight %); and
3-methyl-5-phenylpentan-1-ol (5 to 20 weight %, and more particularly 10 weight %).

The ingredients recited hereinabove as representing components of a liquid fragrance composition of the present invention, preferably represent the total mass of said composition. However, it is possible that said liquid fragrance composition may contain minor amounts of impurities or other ingredients commonly found in perfume formulations. Insofar as impurities or other ingredients are present, preferably they should not make up more than about 0.0001 to about 5 weight % of the liquid fragrance composition.

Liquid fragrance compositions of the present invention are flowable, pourable and mixable with other ingredients commonly used in perfumery across all temperature conditions of storage, transportation and use. A liquid fragrance composition should, upon inspection with the naked eye, contain no solid or crystalline matter, and in particular no solid or crystalline cyclohexylidene phenyl acetonitrile. In a particular embodiment of the present invention, the liquid fragrance compositions are stable, that is, they do not phase separate over a temperature range of −20° C. to 50° C., more particularly −10° C. to 50° C., and still more particularly −5° C. to 50° C.

In a particular embodiment of the present invention the liquid fragrance compositions are stable, that is, they do not phase separate over a temperature range of −20° C. to 50° C., more particularly −10° C. to 50° C., and still more particularly −5° C. to 50° C. when stored in a container for a period of one week to one month.

In a particular embodiment of the present invention the liquid fragrance compositions, in 25 to 250 Kg quantities, are stable, that is, they do not phase separate over a temperature range of −20° C. to 50° C., more particularly −10° C. to 50° C., and still more particularly −5° C. to 50° C., when stored in a container for a period of one week to one month.

In a particular embodiment of the present invention, the liquid fragrance composition as herein above defined is in the form of a stock solution.

A stock solution of the present invention is a liquid fragrance composition, as herein defined, which is to be diluted into other perfumery ingredients to form a fragrance composition, which in turn can be used to perfume a consumer product.

In a more particular embodiment of the present invention, the stock solution is provided in containers containing 25 to 250 l of stock solution.

The liquid fragrance composition as herein defined is useful as a fragrance ingredient in a fragrance composition, which in turn can be used to perfume all manner of personal and household care products.

Fragrance compositions, in addition to the liquid fragrance composition, may contain other perfume ingredients, solvents, carrier materials and other auxiliary agents that are commonly employed in the art. Such ingredients are described in "perfume and flavor materials of natural origin", S. Arctander, Ed. Elizabeth, N.J. 1960; "Perfume and Flavor Chemicals", S. Arctander, Ed. Vol I and II, Allured Publishing Corporation, Carol Stream, USA, 1994; and "International Cosmetic Ingredient Dictionary" $6^{th}$ Ed., the cosmetic, toiletry and fragrance association, Inc. Washington 1995.

Alternatively, the liquid fragrance composition may be employed as the sole fragrance ingredient in personal or household care products.

Liquid fragrance compositions according to the present invention may take the form of an ingredient in a fragrance composition. In this regard, the liquid fragrance composition may be used in amounts substantially similar to those employed by formulators currently using cyclohexylidene phenyl acetonitrile (PEONILE™). In particular, the liquid fragrance compositions may be employed in amounts of 0.2 to 20% by weight based on the weight of a fragrance composition containing same. Consumer products include, in particular household and personal care products, include but are not limited to solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e. g. intended for textile, dish or hard-surface treatment, whether they are intended for domestic or industrial use. Other perfumed articles include fabric refreshers, ironing waters, papers, wipes or bleaches.

In another aspect of the present invention there is provided a method of rendering cyclohexylidene phenyl acetonitrile in liquid form for a period of up to 1 month at a temperature −20° C. to 50° C. more particularly −10° C. to 50° C., and still more particularly −5° C. to 50° C., comprising the step of mixing it with a component A and/or a component B as hereinabove defined, to form a liquid mixture consisting of cyclohexylidene phenyl acetonitrile and a component A and/or a component B.

In order to further illustrate the invention and the advantages thereof, the following example is provided.

EXAMPLE 1

Test samples were prepared by mixing cyclohexylidene phenyl acetonitrile with various amounts of additives, using a Chemspeed mixing robot. The test samples had a size of 25 ml and were stored at 5 degrees centigrade for 1 week before being visually inspected.

Samples that remained visibly liquid under these conditions were seeded with a spatula tip of solid cyclohexylidene phenyl acetonitrile, and again stored at 5 degrees centigrade for 1 week.

Finally, those samples that remained visibly liquid under these conditions were submitted to a temperature of minus 20 degrees centigrade for 1 week, before being subjected again to visual inspection.

A binary mixture of cyclohexylidene phenyl acetonitrile and cyclohexyl salicylate (50/50 wt %) remained liquid under all test conditions.

A similar result was achieved with a ternary mixture of cyclohexylidene phenyl acetonitrile, cyclohexyl salicylate and benzyl alcohol.

A similar result was also observed with a ternary mixture of cyclohexylidene phenyl acetonitrile, cyclohexyl salicylate and 3-methyl-5-phenylpentan-1-ol.

Mixtures of cyclohexylidene phenyl acetonitrile and PETALIA™ had crystallised when inspected after 1 week storage at 5 degree centigrade.

A ternary mixture of cyclohexylidene phenyl acetonitrile, phenyl ethyl alcohol and cyclohexanol was liquid upon inspection after 1 week, but after seeding and storage for a further week, it had crystallised. A similar result was observed with binary mixtures of cyclohexylidene phenyl acetonitrile, and iso-propyl alcohol.

The invention claimed is:

1. A liquid fragrance composition consisting of:
   cyclohexylidene phenyl acetonitrile;
   and a component A, which is one or more ingredients selected from the group consisting of:
      cyclohexyl salicylate, and,
      3-methyl-5-phenyl-pentan-1-ol;
   and a component B, which is one or more ingredients selected from the group consisting of:
      6-ethyl-3-methyl-6-octen-1-ol,
      dimethyl benzyl carbinol,
      5,6,7-trimethyl-2,5-octadiene-4-one,
      phenyl ethyl 2,2 dimethylpropanoate,
      2-methylphenyl ethyl alcohol,
      2-methyl-5-phenyl-pentan-1-ol,
      2-methyl-4-methylene-6-phenyl-tetrahydro-2H-pyran,
      diphenyl oxide,
      1-hydroxy-2-(I-methyl-1-hydroxyethyl)-5-methylcyclohexane),
      3-methyl-2-phenylbut-2-enenitrile,
      (Z)-2-phenylhex-2-enenitrile,
      benzyl alcohol, 1-hexanol,
      1-heptanol,
      1-octanol,
      cyclohexanol,
      cyclohexyl propanol,
      methyl phenyl carbinol,
      phenyl ethyl alcohol,
      dimethyl benzyl carbinol, and,
      a glycol ether.

2. A liquid fragrance composition according to claim 1, herein component B is a glycol ether selected from the group of consisting of:
   propylene glycol,
   dipropylene glycol,
   1-methoxy-2-propanol, and,
   2-(2-methoxypropoxy)propan-1-ol.

3. A liquid fragrance composition according to claim 1 wherein:
   cyclohexylidene phenyl acetonitrile comprises from about 40% by weight to about 95% by weight of the liquid fragrance composition.

4. A liquid fragrance composition according to claim 1 wherein:
   component A comprises from about 5% by weight to about 60% by weight of the liquid fragrance composition.

5. A liquid fragrance composition according to claim 1 wherein:
   component B comprises from about 5% by weight to about 25% by weight of the liquid fragrance composition.

6. A liquid fragrance composition according to claim 1, which consists of:
   about 40% by weight to about 95% by weight of cyclohexylidene phenyl acetonitrile, and,
   about 20% by weight to about 60% by weight of cyclohexyl salicylate.

7. A liquid fragrance composition according to claim 1, wherein the liquid fragrance composition does not phase separate over a temperature range of −20° C. to 50° C. for a period of from one week to a period of one month.

8. A stock solution comprising a liquid fragrance composition according to claim 1.

9. A personal care product or a household care product comprising a liquid fragrance composition according to claim 1.

10. A method of rendering cyclohexylidene phenyl acetonitrile in liquid form for a period of up to 1 month at a temperature −20° C. to 50° C., comprising the step of:
   mixing cyclohexylidene phenyl acetonitrile with at least one component A ingredient with at least one component B ingredient as defined in claim 1, to thereby form a liquid mixture therefrom.

11. A liquid fragrance composition according to claim 1, wherein the compositions are flowable and pourable liquids which, upon inspection with the naked eye, contain no solid or crystalline cyclohexylidene phenyl acetonitrile.

12. A liquid fragrance composition according to claim 1, wherein the composition does not phase separate over a temperature range of −20° C. to 50° C.

13. A liquid fragrance composition according to claim 11, wherein the composition does not phase separate over a temperature range of −10° C. to 50° C.

14. A liquid fragrance composition according to claim 11, wherein the composition does not phase separate over a temperature range of −5° C. to 50° C.

* * * * *